(12) United States Patent
Thaning

(10) Patent No.: US 8,431,723 B2
(45) Date of Patent: Apr. 30, 2013

(54) RADICALS AND THEIR USE AS PARAMAGNETIC AGENTS IN A DNP PROCESS

(75) Inventor: Mikkel Thaning, Oslo (NO)

(73) Assignee: GE Healthcare AS, Oslo (NO)

( * ) Notice: Subject to any disclaimer, the term of this patent is extended or adjusted under 35 U.S.C. 154(b) by 1457 days.

(21) Appl. No.: 11/572,654

(22) PCT Filed: Jul. 28, 2005

(86) PCT No.: PCT/NO2005/000283
§ 371 (c)(1),
(2), (4) Date: Jan. 25, 2007

(87) PCT Pub. No.: WO2006/011811
PCT Pub. Date: Feb. 2, 2006

(65) Prior Publication Data
US 2009/0214432 A1   Aug. 27, 2009

(30) Foreign Application Priority Data

Jul. 30, 2004 (NO) .................................. 20043227

(51) Int. Cl.
*C07D 339/06* (2006.01)
*A61K 49/00* (2006.01)
(52) U.S. Cl.
USPC .............................. 549/31; 424/9.1; 424/9.3

(58) Field of Classification Search ............... 424/9.1, 424/9.3; 549/31
See application file for complete search history.

(56) References Cited

U.S. PATENT DOCUMENTS 6,013,810 A * 1/2000 Thaning .................... 549/31

FOREIGN PATENT DOCUMENTS

| WO | 91/12024 | 8/1991 |
|---|---|---|
| WO | 96/39367 | 12/1996 |
| WO | 98/39277 | 9/1998 |
| WO | 99/35508 | 7/1999 |

OTHER PUBLICATIONS

PCT/NO2005/000283 ISR and Written Opinion dated Apr. 4, 2006.
Wolber, J, et.al., "Generating highly polarized nuclear spins in solution using dynamic nuclear polarization" Nuclear Instruments & Methods in Physics, Research Section—A: Accelerators, Spectrometers, Detectors and Associated Equipment, Elsevier, Amsterdam, NL, vol. 526, No. 1-2. Kime 21.2-4. pp. 183-181, 2004.

* cited by examiner

*Primary Examiner* — Michael G Hartley
*Assistant Examiner* — Jagadishwar Samala
(74) *Attorney, Agent, or Firm* — Jean K. Testa

(57) ABSTRACT

The invention relates to new radicals, their use as paramagnetic agents in a method for the dynamic nuclear polarisation and a method for the dynamic nuclear polarisation of compounds comprising carboxyl groups.

4 Claims, No Drawings

RADICALS AND THEIR USE AS PARAMAGNETIC AGENTS IN A DNP PROCESS

This application is a filing under 35 U.S.C. 371 of international application number PCT/NO2005/000283, filed July 28, 2005, which claims priority to application number 20043227 filed July 30, 2004, in Norway the entire disclosure of which is hereby incorporated by reference.

The invention relates to new radicals, their use as paramagnetic agents in a method for the dynamic nuclear polarisation and a method for the dynamic nuclear polarisation of compounds comprising carboxyl groups.

Magnetic resonance (MR) imaging (MRI) is a imaging technique that has become particularly attractive to physicians as it allows for obtaining images of a patients body or parts thereof in a non-invasive way and without exposing the patient and the medical personnel to potentially harmful radiation such as X-ray. Because of its high quality images, MRI is the favourable imaging technique of soft tissue and organs and it allows for the discrimination between normal and diseased tissue, for instance tumours and lesions.

MR tumour imaging may be carried out with or without MR contrast agents. On an MR image taken without contrast agent, tumours from about 1-2 centimetres in size and larger will show up fairly clearly. However, contrast-enhanced MRI enables much smaller tissue changes, i.e. much smaller tumours to be detected which makes contrast-enhanced MR imaging a powerful tool for early stage tumour detection and detection of metastases.

Several types of contrast agents have been used in MR tumour imaging. Water-soluble paramagnetic metal chelates, for instance gadolinium chelates like Omniscan™ (Amersham Health) are widely used MR contrast agents. Because of their low molecular weight they rapidly distribute into the extracellular space (i.e. the blood and the interstitium) if administered into the vasculature. They are also cleared relatively rapidly from the body. Gadolinium chelates have been found to be especially useful in increasing the detection rate of metastases, small tumours, and improving tumour classification, the latter by allowing the differentiation of vital tumour tissue (well perfused and/or impaired blood-brain-barrier) from central necrosis and from surrounding oedema or macroscopically uninvolved tissue (see for instance C. Claussen et al., Neuroradiology 1985; 27: 164-171).

Blood pool MR contrast agents on the other hand, for instance superparamagnetic iron oxide particles, are retained within the vasculature for a prolonged time. They have proven to be extremely useful to enhance contrast in the liver but also to detect capillary permeability abnormalities, e.g. "leaky" capillary walls in tumours for example as a result of angiogenesis.

Despite the undisputed excellent properties of the aforementioned contrast agents their use is not without any risks. Although paramagnetic metal chelate complexes have usually high stability constants, it is possible that toxic metal ions are released in the body after administration. Further, these type of contrast agents show poor specificity.

WO-A-99/35508 discloses a method of MR investigation of a patient using a hyperpolarised solution of a high $T_1$ agent as MRI contrast agent. The term "hyperpolarisation" means enhancing the nuclear polarisation of NMR active nuclei present in the high $T_1$ agent, i.e. nuclei with non-zero nuclear spin, preferably $^{13}$C- or $^{15}$N-nuclei. Upon enhancing the nuclear polarisation of NMR active nuclei, the population difference between excited and ground nuclear spin states of these nuclei are significantly increased and thereby the MR signal intensity is amplified by a factor of hundred and more. When using a hyperpolarised $^{13}$C- and/or $^{15}$N-enriched high $T_1$ agent, there will be essentially no interference from background signals as the natural abundance of $^{13}$C and/or $^{15}$N is negligible and thus the image contrast will be advantageously high. A variety of possible high $T_1$ agents suitable for hyperpolarisation and subsequent use as MR contrast agents are disclosed including but not limited to non-endogenous and endogenous compounds like acetate, pyruvate, oxalate or gluconate, sugars like glucose or fructose, urea, amides, amino acids like glutamate, glycine, cysteine or aspartate, nucleotides, vitamins like ascorbic acid, penicillin derivates and sulfonamides. It is further stated that intermediates in metabolic cycles such as the citric acid cycle like fumaric acid and pyruvic acid are preferred contrast agents for the imaging of metabolic activity.

It has to be stressed that the signal of a hyperpolarised contrast agent decays due to relaxation and—upon administration to the patient's body—dilution. Hence the $T_1$ value of the contrast agents in biological fluids (e.g. blood) must be sufficiently long to enable the agent to be distributed to the target site in the patient's body in a highly hyperpolarised state. Apart from the contrast agent having a high $T_1$ value, it is extremely favourable to achieve a high polarisation level.

Several hyperpolarising techniques are disclosed in WO-A-99/35508 one of them is the dynamic nuclear polarisation (DNP) technique whereby polarisation of the sample is effected by a paramagnetic compound, the so-called paramagnetic agent or DNP agent. During the DNP process, energy, normally in the form of microwave radiation, is provided, which will initially excite the paramagnetic agent. Upon decay to the ground state, there is a transfer of polarisation from the unpaired electron of paramagnetic agent to the NMR active nuclei of the sample. Generally, a moderate or high magnetic field and a very low temperature are used in the DNP process, e.g. by carrying out the DNP process in liquid helium and a magnetic field of about 1 T or above. Alternatively, a moderate magnetic field and any temperature at which sufficient polarisation enhancement is achieved may be employed. The DNP technique is for example described in WO-A-98/58272 and in WO-A-01/96895, both of which are included by reference herein.

The paramagnetic agent plays a decisive role in the DNP process and its choice has a major impact on the level of polarisation achieved. A variety of paramagnetic agents—in WO-A-99/35508 denoted as "OMRI contrast agents"—is known, for instance oxygen-based, sulfur-based or carbon-based organic free radicals or magnetic particles referred to in WO-A-99/35508, WO-A-88/10419, WO-A-90/00904, WO-A-91/12024, WO-A-93/02711 or WO-A-96/39367.

We have now surprisingly found that the use of certain radicals as paramagnetic agents in the dynamic nuclear polarisation of compounds comprising carboxyl groups allows for obtaining remarkably high polarisation levels.

Thus, viewed from one aspect, the present invention provides a method for the dynamic nuclear polarisation (DNP) of a compound comprising one or more carboxyl groups characterized in that a radical of the formula (I)

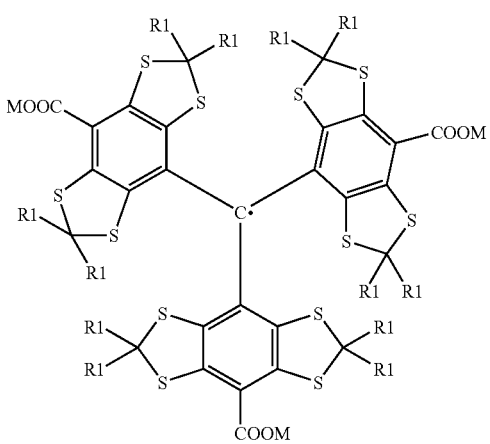

wherein
M represents hydrogen or one equivalent of a cation; and
R1 which is the same or different represents a straight chain or branched $C_1$-$C_6$-alkyl group or a group —$(CH_2)_n$—X—R2, wherein n is 1, 2 or 3; X is O or S and R2 is a straight chain or branched $C_1$-$C_4$-alkyl group is used as paramagnetic agent in said DNP process.

The method according to the invention leads to high polarisation levels in the compounds to be polarised. Hyperpolarisation of compounds that play a role in the metabolic processes in the human and non-human animal body is of great interest, as these hyperpolarised compounds may be used to get information about the metabolic state of a tissue in an in vivo MR investigation, i.e. they are potentially useful as imaging agents for in vivo MR imaging of metabolic activity. Information of the metabolic status of a tissue might for instance be used to discriminate between healthy and tumour tissue, thus rendering hyperpolarised compounds that play a role in metabolic processes potentially useful as imaging agents for in vivo MR tumour imaging.

Many of the compounds that play a role in the metabolic processes in the human or non-human animal body display a high chemical reactivity. We have now found that the radicals of formula (I) are especially useful in the DNP of such compounds as the radicals of formula (I) show very low reactivity towards these types of compounds. Further, it has been found that an intimate contact between the radical of the formula (I) and the compound to be polarised leads to an improvement in the level of polarisation. The solubility of a radical is to a considerable extent dictated by the pH in the dissolution medium and we have found that the radicals of formula (I) have good solubility at a pH range particularly useful in the formulation of these types of compounds. In particular, compounds that play a role in the metabolic process often comprise one or more carboxyl groups. Radicals of formula (I) are found to be stable towards compounds comprising carboxyl groups and the radicals are either easily soluble in compounds comprising carboxyl groups or a solution of a radical of formula (I) and a compound comprising carboxyl groups can be easily prepared using appropriate solvents or solvent mixtures.

In a preferred embodiment, a radical of formula (I) is used in the method according to the invention wherein M represents hydrogen or one equivalent of a physiologically tolerable cation. The term "physiologically tolerable cation" denotes a cation that is tolerated by the human or non-human animal living body. Preferably, M represents hydrogen or an alkali cation, an ammonium ion or an organic amine ion, for instance meglumine. Most preferably, M represents hydrogen or sodium.

In a further preferred embodiment, a radical of formula (I) is used in the method according to the invention wherein R1 is the same, more preferably a straight chain or branched $C_1$-$C_4$-alkyl group, most preferably methyl, ethyl or isopropyl.

In a further preferred embodiment, a radical of formula (I) is used in the method according to the invention wherein R1 is the same or different, preferably the same and represents —$CH_2$—$OCH_3$, —$CH_2$—$OC_2H_5$, —$CH_2$—$CH_2$—$OCH_3$, —$CH_2$—$SCH_3$, —$CH_2$—$SC_2H_5$ or —$CH_2$—$CH_2$—$SCH_3$, most preferably —$CH_2$—$CH_2$—$OCH_3$.

In a more preferred embodiment, M represents hydrogen or sodium and R1 is the same and represents —$CH_2$—$CH_2$—$OCH_3$.

The radicals used in the method of the invention may be synthesized as described in detail in WO-A-91/12024 and WO-A-96/39367. Briefly, the radicals may be synthesized by reacting three molar equivalents of a metallated monomeric aryl compound with one molar equivalent of a suitably protected carboxylic acid derivative to form a trimeric intermediate. This intermediate is metallated and subsequently reacted with e.g. carbon dioxide to result in a tri-carboxylic trityl carbinol which, in a further step, is treated with a strong acid to generate a triarylmethyl cation. This cation is then reduced to form the stable trityl radical.

For the synthesis of the radical of formula (I), wherein M is hydrogen or sodium and R1 is the same and represents —$CH_2$—$CH_2$—$OCH_3$, the following reaction schemes and Example 1 may be used, respectively.

Reaction scheme 1:

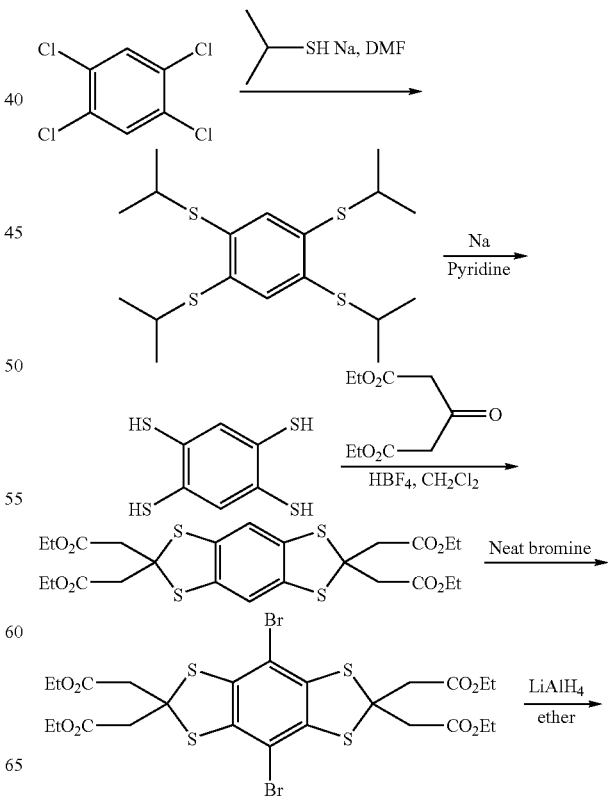

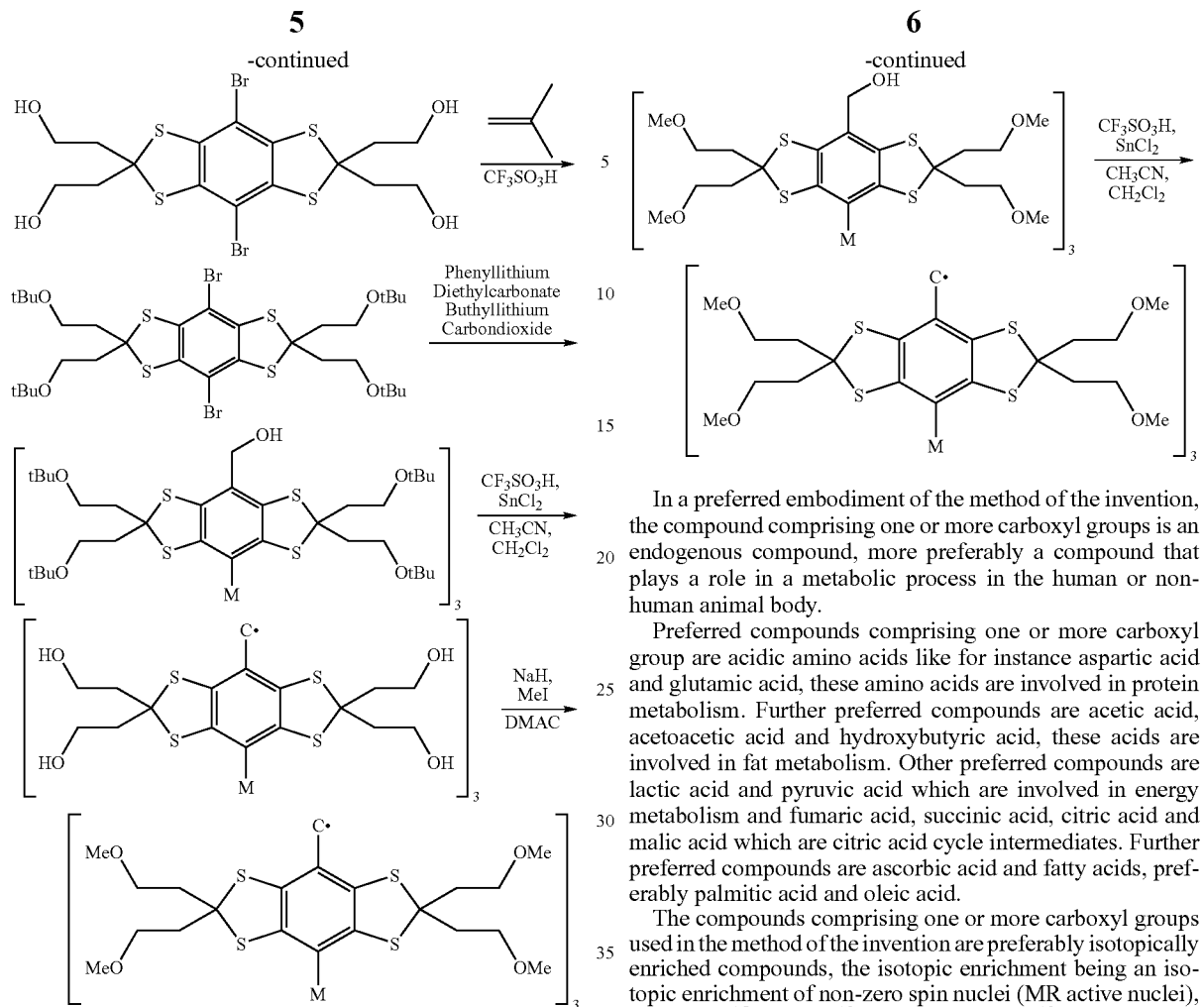

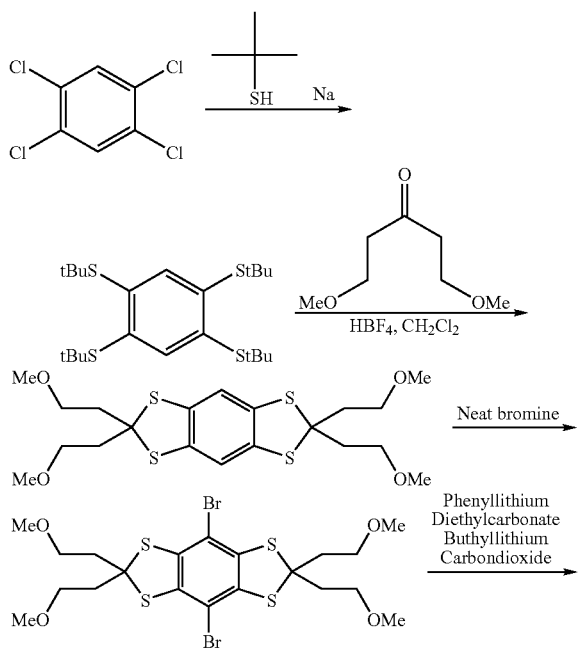

Reaction scheme 2:

In a preferred embodiment of the method of the invention, the compound comprising one or more carboxyl groups is an endogenous compound, more preferably a compound that plays a role in a metabolic process in the human or non-human animal body.

Preferred compounds comprising one or more carboxyl group are acidic amino acids like for instance aspartic acid and glutamic acid, these amino acids are involved in protein metabolism. Further preferred compounds are acetic acid, acetoacetic acid and hydroxybutyric acid, these acids are involved in fat metabolism. Other preferred compounds are lactic acid and pyruvic acid which are involved in energy metabolism and fumaric acid, succinic acid, citric acid and malic acid which are citric acid cycle intermediates. Further preferred compounds are ascorbic acid and fatty acids, preferably palmitic acid and oleic acid.

The compounds comprising one or more carboxyl groups used in the method of the invention are preferably isotopically enriched compounds, the isotopic enrichment being an isotopic enrichment of non-zero spin nuclei (MR active nuclei), preferably $^{15}N$ and/or $^{13}C$, more preferably $^{13}C$. The isotopic enrichment may include either selective enrichments of one or more sites within the compound molecule or uniform enrichment of all sites. Enrichment can for instance be achieved by chemical synthesis or biological labelling, both methods are known in the art and appropriate methods may be chosen depending on the compound to be isotopically enriched.

Preferably, the compound comprising one or more carboxyl groups used in the method of the invention is isotopically enriched in only one position of the molecule, preferably with an enrichment of at least 10%, more suitably at least 25%, more preferably at least 75% and most preferably at least 90%. Ideally, the enrichment is 100%.

The optimal position for isotopic enrichment in the compound comprising one or more carboxyl groups used in the method of the invention is dependent on the relaxation time of the MR active nuclei. Preferably, compounds are isotopically enriched in positions with long $T_1$ relaxation time. $^{13}C$-enriched compounds enriched at a carboxyl-C-atom, a carbonyl-C-atom or a quaternary C-atom are preferably used. If pyruvic acid is polarised according to the method of the invention, it may be isotopically enriched at the C1-position ($^{13}C_1$-pyruvic acid), at the C2-position ($^{13}C_2$-pyruvic acid), at the C3-position ($^{13}C_3$-pyruvic acid), at the C1- and the C2-position ($^{13}C_{1,2}$-pyruvic acid), at the C1- and the C3-position ($^{13}C_{1,3}$-pyruvic acid), at the C2- and the C3-position ($^{13}C_{2,3}$-pyruvic acid) or at the C1-, C2- and C3-position ($^{13}C_{1,2,3}$-pyruvic acid); the C1-position being the preferred one for the $^{13}C$ isotopic enrichment.

Several methods for the synthesis of $^{13}C$-pyruvic acid are known in the art. Briefly, Seebach et al., Journal of Organic Chemistry 40(2), 1975, 231-237 describe a synthetic route that relies on the protection and activation of a carbonyl-containing starting material as an S,S-acetal, e.g. 1,3-dithian or 2-methyl-1,3-dithian. The dithian is metallated and reacted with a methyl-containing compound and/or $^{13}CO_2$. By using the appropriate isotopically enriched $^{13}C$-component as outlined in this reference, it is possible to obtain $^{13}C_1$-pyruvic acid, $^{13}C_2$-pyruvic acid or $^{13}C_{1,2}$-pyruvic acid. A different synthetic route starts from acetic acid, which is first converted into acetyl bromide and then reacted with $Cu^{13}CN$. The nitril obtained is converted into pyruvic acid via the amide (see for instance S. H. Anker et al., J. Biol. Chem. 176 (1948), 1333 or J. E. Thirkettle, Chem Commun. (1997), 1025). Further, $^{13}C$-pyruvic acid may be obtained by protonating commercially available sodium $^{13}C$-pyruvate, e.g. by the method described in U.S. Pat. No. 6,232,497.

In a further preferred embodiment, the compounds comprising one or more carboxyl groups used in the method of the invention are liquids at room temperature, like for instance pyruvic acid or lactic acid and the radical of formula (I) is chosen as such that it is soluble in the liquid compound. This will result in a concentrated compound/radical solution without the need of further solvents being present in the mixture. In a most preferred embodiment of the method of the invention, the compound comprising one or more carboxyl groups is $^{13}C$-pyruvic acid, preferably $^{13}C_1$-pyruvic acid and the radical of formula (I) is a radical wherein M is hydrogen or sodium and R1 is the same and represents —$CH_2$—$CH_2$—$OCH_3$.

If the compound comprising one or more carboxyl groups used in the method of the invention is a solid at room temperature, it may be melted and the melted compound may then be mixed with the radical of formula (I) to dissolve the radical in the melted compound. Subsequently, the solution is cooled and/or frozen, preferably in such a way that crystallization of the compound to be polarised is prohibited. Cooling/freezing may be achieved by methods known in the art, e.g. by freezing the solution in liquid nitrogen or by simply placing it in the DNP polariser, where liquid helium will freeze the solution. In another embodiment, the solid compound comprising one or more carboxyl groups may be dissolved in an adequate solvent or solvent mixture, preferably in a solvent which is a good glass former and does prevent crystallization upon cooling/freezing. Suitable glass formers are for instance glycerol, propanediol or glycol. The dissolved compound is then mixed with the radical of formula (I) and the solution is cooled and/or frozen for the DNP process. Intimate mixing can be further promoted by several means known in the art, such as stirring, vortexing or sonification.

The DNP technique is for instance described in WO-A-98/58272 and in WO-A-01/96895, both of which are included by reference herein. Generally, a moderate or high magnetic field and a very low temperature are used in the DNP process, e.g. by carrying out the DNP process in liquid helium and a magnetic field of about 1 T or above. Alternatively, a moderate magnetic field and any temperature at which sufficient polarisation enhancement is achieved may be employed. In a preferred embodiment, the DNP process is carried out in liquid helium and a magnetic field of about 1 T or above. Suitable polarisation units are for instance described in WO-A-02/37132. In a preferred embodiment, the polarisation unit comprises a cryostat and polarising means, e.g. a microwave chamber connected by a wave guide to a microwave source in a central bore surrounded by magnetic field producing means such as a superconducting magnet. The bore extends vertically down to at least the level of a region P near the superconducting magnet where the magnetic field strength is sufficiently high, e.g. between 1 and 25 T, for polarisation of the $^{13}C$ nuclei to take place. The sample bore is preferably sealable and can be evacuated to low pressures, e.g. pressures in the order of 1 mbar or less. A sample (i.e. the frozen compound/radical mixture) introducing means such as a removable sample-transporting tube can be contained inside the bore and this tube can be inserted from the top of the bore down to a position inside the microwave chamber in region P. Region P is cooled by liquid helium to a temperature low enough to for polarisation to take place, preferably temperatures of the order of 0.1 to 100 K, more preferably 0.5 to 10 K, most preferably 1 to 5 K. The sample introducing means is preferably sealable at its upper end in any suitable way to retain the partial vacuum in the bore. A sample-retaining container, such as a sample-retaining cup, can be removably fitted inside the lower end of the sample introducing means. The sample-retaining container is preferably made of a lightweight material with a low specific heat capacity and good cryogenic properties such, e.g. KelF (polychlorotrifluoroethylene) or PEEK (polyetheretherketone) and it may be designed in such a way that it can hold more than one sample.

The sample is inserted into the sample-retaining container, submerged in the liquid helium and irradiated with microwaves, preferably at a frequency about 94 GHz at 200 mW. The level of polarisation may be monitored by for instance acquiring solid state $^{13}C$— and/or $^{15}N$-NMR signals of the sample during microwave irradiation, depending on the compound to be polarised. Generally, a saturation curve is obtained in a graph showing NMR signal vs. time. Hence it is possible to determine when the optimal polarisation level is reached.

If the compound polarised according to the method of the invention is used as an MR imaging agent, it is preferably transferred from a solid hyperpolarised compound to a liquid hyperpolarised compound, either by dissolving it after the DNP process in an appropriate solvent, e.g. a physiologically tolerable aqueous carrier like a buffer, the dissolution being for instance described in WO-A-02/37132 or by melting it, as for instance described in WO-A-02/36005.

Further, the radical and or reaction products thereof may be removed from the liquid hyperpolarised compound. Methods usable to partially, substantially or completely remove the radical and/or reaction products thereof are known in the art. Generally, the methods applicable depend on the nature of the radical and/or its reaction products. Upon dissolution of the solid hyperpolarised compound, the radical might precipitate and it may easily be separated from the liquid by filtration. If no precipitation occurs, the radical may be removed by chromatographic separation techniques, e.g. liquid phase chromatography like reversed phase, straight phase or ion exchange chromatography or by extraction.

As radicals of formula (I) have a characteristic UV/visible absorption spectrum, it is possible to use UV/visible absorption measurement as a method to check for its existence in the liquid after its removal. In order to obtain quantitative results, i.e. the concentration of the radical present in the liquid, the optical spectrometer can be calibrated such that absorption at a specific wavelength form a sample of the liquid yields the corresponding radical concentration in the sample. Removal of the radical and/or reaction products thereof is especially preferred if the liquid hyperpolarised compound is used as a contrast agent for in vivo MR imaging of a human or non-human animal body.

Yet another aspect of the invention are new radicals of the formula (I),

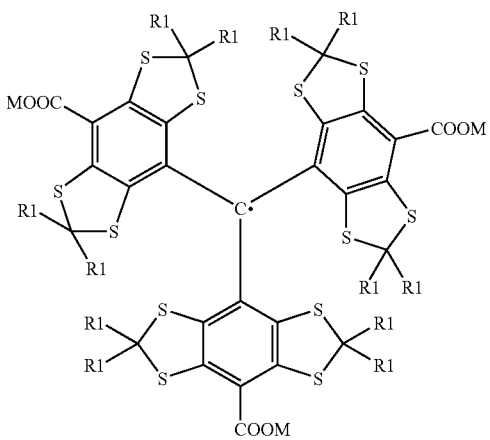

wherein

M represents hydrogen or one equivalent of a cation; and

R1 which is the same or different represents —(CH$_2$)$_n$—X—R2, wherein n is 1, 2 or 3;

X is O or S; and

R2 is a straight chain or branched C$_1$-C$_4$-alkyl group.

Preferred radicals of formula (I) are the radicals wherein M represents hydrogen or one equivalent of a physiologically tolerable cation, preferably an alkali cation, an ammonium ion or an organic amine ion. Further preferred radicals of formula (I) are the radicals wherein R1 is the same and represents —CH$_2$—OCH$_3$, —CH$_2$—OC$_2$H$_5$, —CH$_2$—CH$_2$—OCH$_3$, —CH$_2$—SCH$_3$, —CH$_2$—SC$_2$H$_5$ or —CH$_2$—CH$_2$—SCH$_3$, most preferably —CH$_2$—CH$_2$—OCH$_3$. Most preferred radicals of formula (I) are the radicals wherein M represents hydrogen or one equivalent of a physiologically tolerable cation, preferably sodium and R1 is the same and represents —CH$_2$—CH$_2$—OCH$_3$.

Yet another aspect of the invention are compositions comprising a compound comprising one or more carboxyl groups and a new radical of formula (I), i.e. a radical of formula (I)

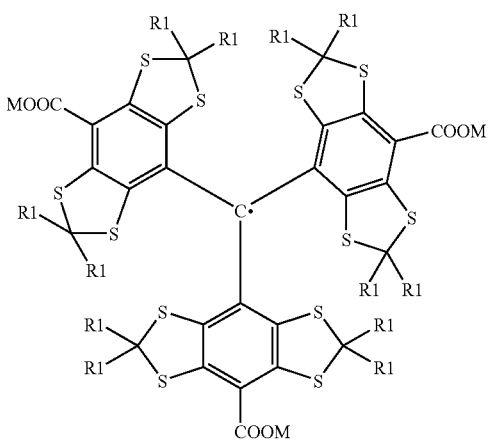

wherein

M represents hydrogen or one equivalent of a cation; and

R1 which is the same or different represents —(CH$_2$)$_n$—X—R2, wherein n is 1, 2 or 3;

X is O or S; and

R2 is a straight chain or branched C$_1$-C$_4$-alkyl group.

EXAMPLES

Example 1

Synthesis of Tris(8-carboxy-2,2,6,6-(tetra(methoxyethyl)benzo-[1,2-4,5']bis-(1,3)dithiole-4-yl)methyl sodium salt 10 g (70 mmol) Tris(8-carboxy-2,2,6,6-(tetra(hydroxyethyl)benzo-[1,2-4,5']bis(1,3)-dithiole-4-yl)methyl sodium salt which had been synthesized according to Example 7 of WO-A1-98/39277 were suspended in 280 ml dimethylacetamide under an argon atmosphere. Sodium hydride (2.75 g) followed by methyl iodide (5.2 ml) was added and the reaction which is slightly exothermic was allowed to proceed for 1 hour in a 34° C. water bath for 60 min. The addition of sodium hydride and methyl iodide was repeated twice with the same amounts of each of the compounds and after the final addition, the mixture was stirred at room temperature for 68 hours and then poured into 500 ml water. The pH was adjusted to pH>13 using 40 ml of 1 M NaOH (aq) and the mixture was stirred at ambient temperature for 15 hours to hydrolyse the formed methyl esters. The mixture was then acidified using 50 ml 2 M HCl (aq) to a pH of about 2 and 3 times extracted the ethyl acetate (500 ml and 2×200 ml). The combined organic phase was dried over Na$_2$SO$_4$ and then evaporated to dryness. The crude product (24 g) was purified by preparative HPLC using acetonitrile/water as eluents. The collected fractions were evaporated to remove acetonitrile. The remaining water phase was extracted with ethyl acetate and the organic phase was dried over Na$_2$SO$_4$ and then evaporated to dryness. Water (200 ml) was added to the residue and the pH was carefully adjusted with 0.1 M NaOH (aq) to 7, the residue slowly dissolving during this process. After neutralization, the aqueous solution was freeze dried.

Example 2

Production of Hyperpolarised $^{13}$C-Pyruvate Using $^{13}$C-Pyruvic Acid and the Radical of Example 1

A 20 mM solution was prepared by dissolving 5.0 mg of the radical of Example 1 in $^{13}$C$_1$-pyruvic acid (164 µl). The sample was mixed to homogeneity and an aliquot of the solution (41 mg) was placed in a sample cup and inserted in the DNP polariser.

The sample was polarised under DNP conditions at 1.2 K in a 3.35 T magnetic field under irradiation with microwave (93.950 GHz). After 2 hours the polarisation was stopped and the sample was dissolved using a dissolution device according to WO-A-02/37132 in an aqueous solution of sodium hydroxide and tris(hydroxymethyl)-aminomethane (TRIS) to provide a neutral solution of hyperpolarized sodium $^{13}C_1$-pyruvate. The dissolved sample was rapidly analysed with $^{13}C$-NMR to assess the polarisation and a 19.0% $^{13}C$ polarisation was obtained.

Example 3

Production of Hyperpolarised $^{13}C$-Pyruvate Using $^{13}C$-Pyruvic Acid and the Radical of Example 1

A 15 mM solution was prepared by dissolving the radical of Example 1 (209.1 mg) in a mixture of $^{13}C_1$-pyruvic acid (553 mg) and unlabelled pyruvic acid (10.505 g). The sample was mixed to homogeneity and an aliquot of the solution (2.015 g) was placed in a sample cup and inserted in the DNP polariser.

The sample was polarised under DNP conditions at 1.2 K in a 3.35 T magnetic field under irradiation with microwave (93.950 GHz). After 4 hours the polarisation was stopped and the sample was dissolved using a dissolution device according to WO-A-02/37132 in an aqueous solution of sodium hydroxide and tris(hydroxymethyl)aminomethane (TRIS) to provide a neutral solution of hyperpolarized sodium $^{13}C_1$-pyruvate with a total pyruvate concentration of 0.5 M in 100 mM TRIS buffer. In series with the dissolution device a chromatographic column was connected. The column consists of a cartridge (D=38 mm; h=10 mm) containing hydrophobic packing material (Bondesil-C18, 40UM Part #:12213012) supplied by Varian. The dissolved sample was forced through the column which selectively adsorbed the radical. The filtered solution was rapidly analysed with $^{13}C$-NMR to assess the polarisation, 16.5% $^{13}C$ polarisation was obtained. The residual radical concentration was subsequently analysed with a UV spectrophotometer at 469 nm and was determined to be below the detection limit of 0.1 µM.

The invention claimed is:

1. Radicals of the formula (I)

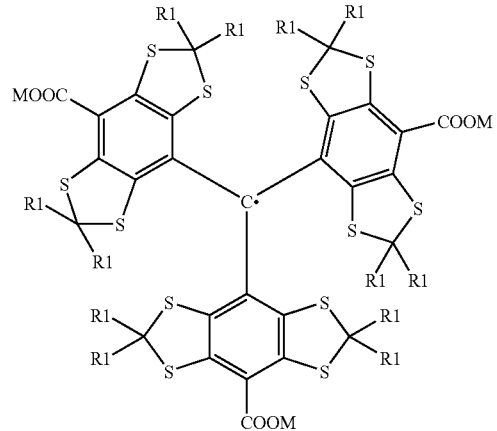

wherein
M represents hydrogen or one equivalent of a cation; and
R1 which is the same or different represents —$(CH_2)_n$—X—R2,
wherein n is 1, 2 or 3;
X is O or S; and
R2 is a straight chain or branched $C_1$-$C_4$-alkyl group.

2. A radical according to claim 1 wherein M represents hydrogen or one equivalent of a physiologically tolerable cation, preferably an alkali cation, an ammonium ion or an organic amine ion.

3. A radical according to claim 1 wherein R1 is the same and represents —$CH_2$—$OCH_3$, —$CH_2$—$OC_2H_5$, —$CH_2$—$CH_2$—$OCH_3$, —$CH_2$—$SCH_3$, —$CH_2$—$SC_2H_5$ or —$CH_2$—$CH_2$—$SCH_3$, most preferably —$CH_2$—$CH_2$—$OCH_3$.

4. A radical according to claim 1 wherein M represents hydrogen or one equivalent of a physiologically tolerable cation, preferably sodium and R1 is the same and represents —$CH_2$—$CH_2$—$OCH_3$.

* * * * *